United States Patent [19]

Holland

[11] 4,026,143
[45] May 31, 1977

[54] ULTRASONIC SENSOR ASSEMBLY

[75] Inventor: Charles L. Holland, Escondido, Calif.

[73] Assignee: General Dynamics Corporation, San Diego, Calif.

[22] Filed: Feb. 23, 1976

[21] Appl. No.: 660,220

[52] U.S. Cl. ............................ 73/67.5 R; 82/21 B; 90/11 R; 408/8
[51] Int. Cl.$^2$ ........................................ G01N 29/00
[58] Field of Search .......... 73/67.5 R, 67.7, 67.5 R, 73/71.5 US; 340/1 R, 3 R, 5 R; 82/21 B; 90/11 R; 408/8

[56] References Cited
UNITED STATES PATENTS

| | | |
|---|---|---|
| 3,190,112 | 6/1965 | Beaujard et al. ............. 73/71.5 US |
| 3,420,097 | 1/1969 | Batterman .................... 73/71.5 US |
| 3,483,795 | 12/1969 | Wranosky ..................... 90/13.5 |
| 3,817,647 | 6/1974 | Lemelson ............................. 408/8 |
| 3,834,256 | 9/1974 | Abbatiello et al. ................ 82/21 B |

*Primary Examiner*—Donald O. Woodiel
*Assistant Examiner*—Stephen A. Kreitman
*Attorney, Agent, or Firm*—John R. Duncan

[57] ABSTRACT

A mounting assembly for supporting an ultrasonic transducer within a machine tool. An ultrasonic tube assembly mounted coaxially within a machine spindle and tool supports an ultrasonic sensor adjacent to the surface being machined during machining. The tube mount includes means for isolating the tube assembly from vibration of the spindle and tool. Real-time thickness measurement of the surface being machined can be obtained by using thickness as measured by the ultrasonic sensor in a conventional feedback loop, controlling tool position.

11 Claims, 2 Drawing Figures

ULTRASONIC SENSOR ASSEMBLY

BACKGROUND OF THE INVENTION

This invention relates in general to a device for real-time thickness measurement during machining and, more specifically, to an improved ultrasonic thickness measuring assembly for such use.

Large integrally stiffened skins machined in one piece from an aluminum billet are gaining widespread use in space vehicles and high-speed aircraft designs. These structures must combine high strength with light weight. Weight penalties are particularly severe in space vehicle applications; in some cases thousands of dollars per pound. Dimensional accuracies on the order of ± 0.005 inch which are commonly required exceed the capability of many milling machines and leave very little allowance for measurement error. Typically, all of a 2.5 inch billet except for a 0.050 skin thickness is milled away, removing some stresses and leaving others. This creates the potential for skin warpage, producing gaps between the machine bed and the face of the billet being machined. As the milling cutter passes over these gaps, undetected thinning of the skin can require scrapping of the entire part.

Further, compensation for machine backlash, tool wear, etc. is not possible. The necessary result is the use of broader tolerances, resulting in greater weight, plus increased waste where the machine goes out of even the broader tolerances.

An attempt has been made to provide real-time thickness measurement by mounting an ultrasonic transducer within the tool. Such a device is disclosed in U.S. Pat. No. 3,483,795 to Wranosky. While this device has several advantages, it has not been found to be fully effective for several reasons. Vibration from the tool spindle and tool, within which the ultrasonic transducers is mounted, make detection of the ultrasonic signal difficult, and at times impossible.

Thus, there is a continuing need for improved means for mounting ultrasonic thickness measuring transducers within machine tools.

OBJECTS OF THE INVENTION

An object, therefore, of this invention is to provide an ultrasonic transducer mounting assembly overcoming the above-noted problems.

Another object of this invention is to provide an ultrasonic transducer mounting assembly resulting in ultrasonic thickness measurements of improved accuracy and reliability.

A further object of this invention is to provide an ultrasonic transducer mounting assembly which substantially eliminates interference from tool or spindle vibration.

SUMMARY OF THE INVENTION

The above objects, and others, are accomplished in accordance with this invention, by a mounting assembly which positions an ultrasonic transducer within a machine tool, the mounting assembly comprising a pair of concentric tubes positioned along the axis of a hollow machine tool and spindle and a means for mounting the tubes on the machine tool assembly so that the tool can rotate around the tubes without transmitting tool or spindle vibration to the tubes. The inner tube is closed at one end by an ultrasonic transducer which is positioned adjacent to the surface being machined. Means are included for directing a tool coolant between the two tubes, over the transducer and onto the workpiece in a substantially bubble-free laminar flow manner.

BRIEF DESCRIPTION OF THE DRAWING

Details of a preferred embodiment of this invention will be further understood upon reference to the drawing, wherein.

DETAILED DESCRIPTION OF THE INVENTION

Figure 1:
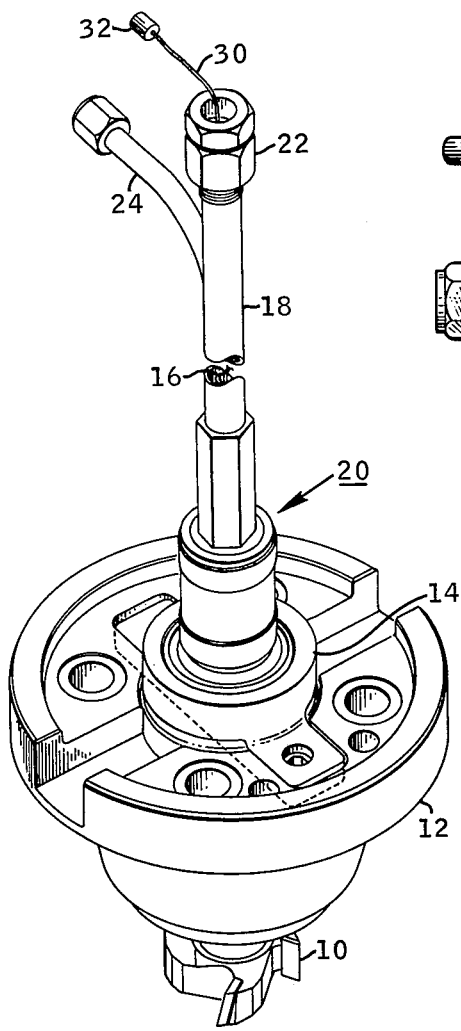
FIG. 1 is a perspective view of the mounting assembly of this invention installed in a milling tool assembly.

Referring now to FIG. 1, there is seen a conventional end milling tool 10 mounted in a conventional tool holder 12 (somewhat simplified, for clarity) which is adapted to mount in the usual manner on the spindle of a milling machine (not shown).

A bearing mount 14 is secured to the upper surface of tool holder 12. An assembly comprising a first inner tube 16 and a second outer tube 18 passes downwardly through bearing mount 14, tool holder 12 and tool 10 and is supported thereon by means of mounting assembly 20. Tubes 16 and 18 have been shortened for clarity, since they ordinarily extend several feet above tool mount 12 so as to reach to the top of the machine spindle when the tool is in use.

A conventional connector 22 holds tubes 16 and 18 in alignment and closes off the space between the tubes. A tube 24 communicating with the annular space between inner tube 16 and outer tube 18 is provided so that a coolant flow may be directed into that space.

Figure 2:
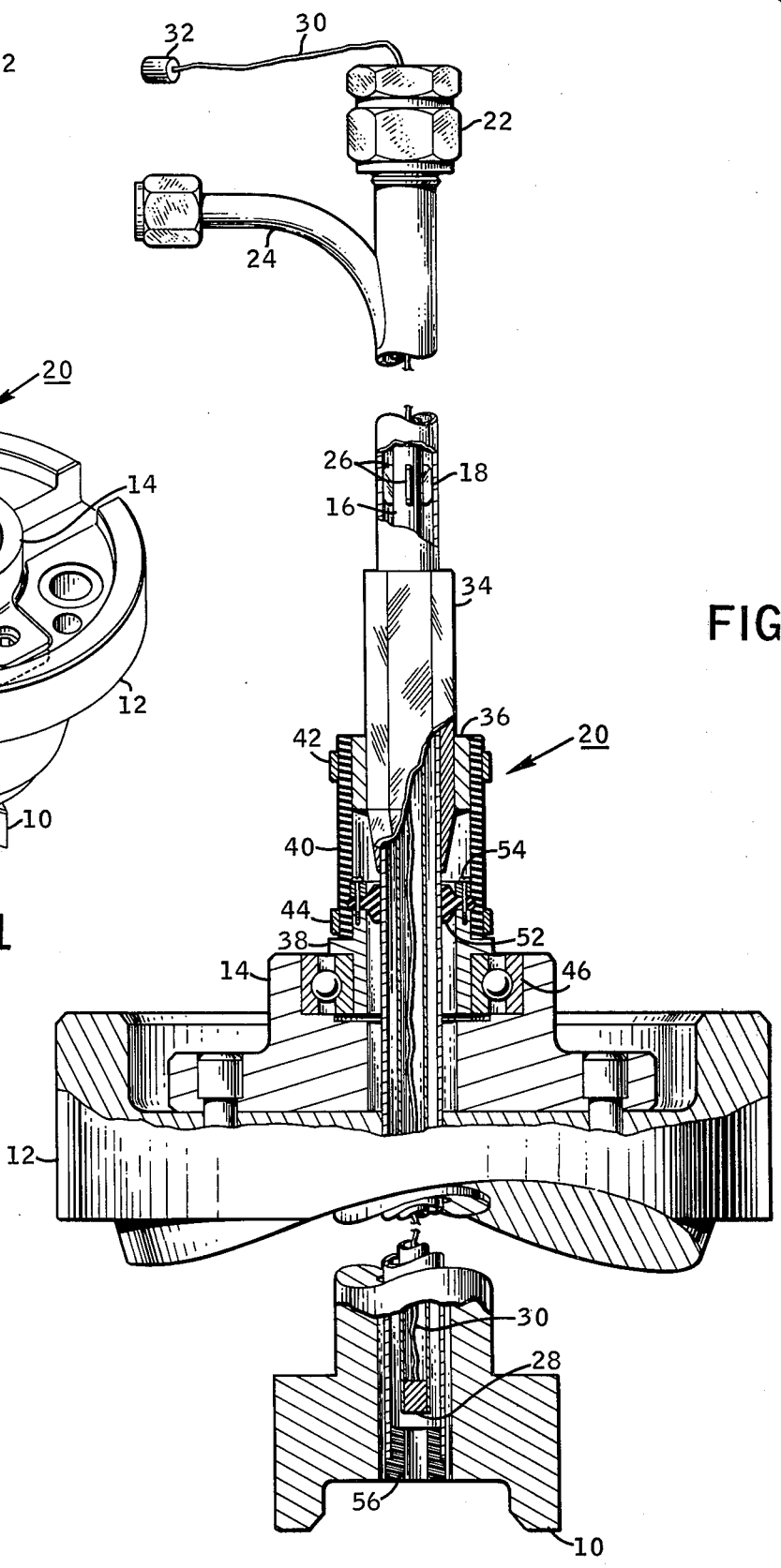
FIG. 2 is an elevation view partly cutaway with portions in section along the plane of the axis of rotation of the tool assembly.

Details of the construction of the mounting assembly are apparent in FIG. 2. The drawing has been broken and shortened to give the largest possible illustration of the novel components for clarity.

First tube 16 is maintained in the proper spaced relationship with second tube 18 by a plurality of spiders or fin-like spacers 26. While only one spider 26 is shown, preferably several are used, spaced about 12 to 18 inches apart. Tubes 16 and 18 and spiders 26 may be fabricated from any suitable material. Stainless steel has been found to be an excellent material, with the individual fins making up spider 26 silver soldered to first tube 16.

Tubes 16 and 18 may have any suitable diameters. Preferably, inner tube 16 has a diameter of from about 0.25 to 0.50 inch to accommodate an ultrasonic transducers of reasonable size without requiring an excessively large opening through the machine tool. Preferably, outer tube 18 has a diameter 0.20 to 0.25 inch greater than that of inner tube 16 to permit a sufficient flow of coolant under reasonable pressure without requiring an undesirably large opening through tool 10.

The lower end of first tube 16 is fitted with an ultrasonic transducer 28. Fluid between tubes 16 and 18 is prevented from entering tube 16. The transducer signal cable 30 passes up tube 16 to a conventional connector 32. Any suitable ultrasonic transducer may be used in this system. A typical suitable transducer, having a frequency of 15 MHz and beam alignment of ±0.5 deg. is available from the Aerotech Lab Division of Bronson Instrument, Inc. Transducer 28 may be spaced any suitable distance from the surface of the workpiece being machined. Preferably, the spacing is from about 0.50 to 0.75 inch. If transducer 28 is too close to the workpiece contact may occur between tube 18 and the workpiece may result, while if the spacing is too great there is a decrease in ultrasonic signal strength. Optimum results have been obtained with the surface of transducer 28 about 0.70 inch from the workpiece surface.

Because of the coolant inlet tube 24 and cable 30, it is necessary that tubes 16 and 18 remain stationary while the tool assembly rotates during assembly. At the same time, the tubes must be maintained at a precise location within the tool assembly. Mounting assembly 20 supports tubes 16 and 18 in place while isolating transducer 28 from vibration coming from tool 10 or the machine spindle (not shown). While it might be possible to allow tubes 16 and 18 to rotate with tool 10, using slip rings for cable 30 and a rotary conduit for coolant flow, additional vibration problems would result if tubes 16 and 18 were rigidly fastened to the tool mount.

A portion 34 of the outer surface of second tube 18 is configured in an other than circular cross-section. While any suitable shape may be used, a hexagonal cross-section is convenient. First sleeve 36 has an inner configuration conforming to the exterior of portion 34 and is a close sliding fit thereon. Thus, if tube 18 is held stationary, the interlocking arrangement of portion 34 and first sleeve 36 will prevent rotation of mounting assembly 20.

First sleeve 36 is connected to second sleeve 38 by means of a flexible tubular member 40. Flexible tubular member 40 may have any suitable dimensions and may be manufactured from any suitable material. Preferably, tube 40 has a length of from about 1.5 to 2.5 inches, an outside diameter of about 1.0 to 1.5 inches and a wall thickness of from about 0.125 to 0.250 inch. Typical materials include natural rubber, vinyl and neoprene. An optimum combination of strength, flexibility and vibration isolation together with resistance to oils and heat is obtained with a neoprene tube having a length of about 1.75 inches, diameter of 1.25 inches and thickness of about 0.125 inch. Tubular member 40 is secured to sleeves 36 and 38 by a pair of pressure rings or straps 42 and 44. Second sleeve 38 is mounted on a bearing 46 (which may be any suitable bearing, such as a conventional ball bearing) which is secured to bearing mount 14 to permit relative rotation between tool holder 12 and mounting assembly 20.

Vibration is further damped by an elastic damping washer 50 which is held to sleeve 38 by a ring 52 and pin 54 arrangement. It has been found that tubular member 40 isolates transducer 28 from most machine vibration, while the addition of washer 52 substantially eliminates such vibration when used in combination with tubular member 40. Washer 50 may typically be formed neoprene sponge rubber.

Besides transducer interference due to vibration, the presence of bubbles in coolant flowing from tube 24, down between tubes 16 and 18 are out under tool 10 tends to produce spurious signals at transducer 28. Therefore, a nozzle 56 is included at the outlet of tube 18, reducing the outlet cross-sectional area to no greater than the cross-sectional area between tubes 16 and 18, and having a cylindrical shape, to direct the coolant fluid in a bubble-free laminar flow column over the face of transducer 28 and onto the workpiece below tool 10. Nozzle 56 is preferably spaced from about 0.125 to 0.250 inch from the workpiece surface for optimum ultrasonic signal strength without danger of contact with the workpiece. While any suitable material may be used for nozzle 56, fluorocarbon resins such as those available from E. I. duPont deNemours, Inc. under the "Teflon" trademarks are preferred because of their chemical resistance to cutting fluids and ease of fabrication.

Any suitable fluid may be used as the combined machining coolant and ultransonic coolant in this system. While water is an ideal medium for ultrasound transmission, it is often impractical since it will promote rust and corrosion. Excellent results are obtained with Pems 11312, a synthetic coolant available from the Pemco Corporation.

In tests, it has been found that with tube 18 ridgidly connected to the inner race of bearing 46, vibration was sufficient to block out the entire transducer signal at a tool rotation speed of less than half that required for efficient machining. With the addition of mounting assembly 20, including flexible tubular member 40 and washer 52, an excellent ultrasonic signal was obtained at all machining speeds.

In operation, transducer 28, generates an ultrasonic pulse train which is transmitted to the workpiece to be measured through the fluid column of machine coolant serving as an ultrasonic couplant. Return echoes from the workpiece are reconverted to electrical signals by the transducer. The electrical signals from the workpiece are typically fed to an ultramicrometer, such as a Model 722A from Erdman Instruments Co., which converts the ultrasonic signals to a digital readout in inches. If desired, signals from the ultrasonic micrometer may also drive a digital printer, which may be designed, for example, to print thickness measurements which are outside of preselected tolerances in red. Also, a conventional feedback loop may be added whereby the numerical control machine controls are adjusted automatically if the measured thickness approaches the tolerance limits. Transducer 28, through cable 30 and connector 32 may be connected to any suitable signal analyzing and thickness measuring circuitry, with or without machine control feedback circuitry. Typical circuitry which could also be used is disclosed in U.S. Pat. No. 3,483,795.

While certain preferred materials, dimensions and arrangements are described in connection with the above description of a preferred embodiment. These may be varied and other arrangements used, where suitable, as discussed above. Other applications, variations and ramifications of this invention will occur to those skilled in the art upon reading this disclosure. These are intended to be included within the scope of this invention as defined by the appended claims.

I claim:

1. A mounting assembly for supporting an ultrasonic transducer within an axial bore a rotatable machine tool assembly which comprises:
   a first tube adapted to be positioned with a hollow rotatable machine tool assembly along the axis of tool rotation;
   an ultrasonic transducer closing one end of said first tube and adapted to be positioned adjacent to the workpiece surface being machined;
   a second tube coaxial with and surrounding said first tube spaced from said first tube by a plurality of spiders;

means to introduce a fluid between said first and second tubes and to cause said fluid to move toward said workpiece surface in a substantially bubble-free laminar flow column;

at least a portion of the outer surface of said second tube having an outer than circular cross-section;

a first sleeve closely surrounding said other than circular cross-section portion and having an inner surface cross-section conforming to said portion; and a flexible tubular member connecting said first sleeve to a second sleeve surrounding but spaced from said second tube;

said second sleeve adapted to be mounted for relative rotation on said rotatable tool assembly by means of a bearing;

whereby said tool assembly may be rotated while said first and second tubes are maintained stationary without significant transfer of vibration from said tool assembly to said first and second tubes.

2. The mounting assembly according to claim 1 further including an elastic damping washer positioned between said second sleeve and the outer surface of a second portion of said second tube.

3. The mounting assembly according to claim 1 further including a nozzle in the end of said second tube adjacent to said workpiece surface between said workpiece surface and said transducer, the opening in said nozzle having a cross-section area substantially equal to the cross-section area between said coaxial first and second tubes along their coextensive length.

4. The mounting assembly according to claim 1 further including an electrical connector extending the length of said first tube adapted to connect said transducer to outside electrical devices.

5. The mounting assembly according to claim 1 further including a plurality of spiders spaced from about 12 to 18 inches apart along said first tube, each spider comprising a plurality of radially arranged fins secured to one of said first and second tubes, each fin positioned substantially parallel to the axis of said tubes.

6. The mounting assembly according to claim 1 wherein said flexible tubular member has a length of from about 1.5 to 2.5 inches, an outside diameter of from about 1.0 to 1.5 inches and a wall thickness of from about 0.125 to 0.250 inch.

7. In an ultrasonic thickness measuring system mounted in a rotatable machine tool assembly which comprises an assembly of coaxial first inner and second outer tubes supported within an axial bore within a machine tool and tool mount, an ultrasonic transducer closing one end of said first tube and positioned adjacent to a workpiece to be machined, said second tube adapted to conduct a cooling fluid to the workpiece and tube support means to maintain said tube assembly stationary during tool rotation, the improvement wherein said tube support means comprises a first sleeve surrounding a portion of said second tube, the inner surface of said first sleeve and the corresponding outer surface of said second tube having close fitting, other than circular, cross-sections; a flexible tubular member connecting said first sleeve to a second sleeve surrounding but spaced from said second tube; said second sleeve mounted on the tool assembly by a bearing which permits relative between said second sleeve and said tool assembly.

8. The improvement according to claim 5 further including an elastic damping washer positioned between said second sleeve and the outer surface of a second portion of said second tube.

9. The improvement according to claim 5 further including a nozzle in the end of the said second tube adjacent to said workpiece surface between said workpiece surface and said transducer, the opening in said nozzle having a cross-section area substantially equal to the cross-section area between said coaxial first and second tubes along their coextensive length.

10. The improvement according to claim 7 further including a plurality of spiders spaced from about 12 to 18 inches apart along said first tube, each spider comprising a plurality of radially arranged fins secured to one of said first and second tubes, each fin positioned substantially parallel to the axis of said tubes.

11. The improvement according to claim 7 wherein said flexible tubular member has a length of from about 1.5 to 2.5 inches, an outside diameter of from about 1.0 to 1.5 inches and a wall thickness of from about 0.125 to 0.250 inch.

* * * * *